US008034462B2

(12) United States Patent
Magne et al.

(10) Patent No.: US 8,034,462 B2
(45) Date of Patent: Oct. 11, 2011

(54) WOOD TREATED BY IMPREGNATION WITH MIXED ANHYDRIDES

(75) Inventors: Michel Magne, Moussy (FR); Silham El Kasmi, Chalons en Champagne (FR); Maxime Dupire, Toulouse (FR); Marie Morard, Toulouse (FR); Carlos Vaca-Garcia, Toulouse (FR); Sophie Thiebaud-Roux, L'Union (FR); Jerome Peydecastaing, Toulouse (FR); Elisabeth Borredon, Tournefeuille (FR); Antoine Gaset, Toulouse (FR)

(73) Assignee: Lapeyre, Aubervilliers (FR)

( * ) Notice: Subject to any disclaimer, the term of this patent is extended or adjusted under 35 U.S.C. 154(b) by 0 days.

(21) Appl. No.: 12/842,290

(22) Filed: Jul. 23, 2010

(65) Prior Publication Data

US 2010/0291398 A1  Nov. 18, 2010

Related U.S. Application Data

(62) Division of application No. 10/510,226, filed as application No. PCT/FR03/01110 on Apr. 9, 2003, now Pat. No. 7,790,239.

(30) Foreign Application Priority Data

Apr. 10, 2002  (FR) ..................................... 02 04448

(51) Int. Cl.
*B32B 21/04* (2006.01)
*B05D 5/00* (2006.01)
*B27K 3/00* (2006.01)

(52) U.S. Cl. ..................... 428/537.1; 427/325; 427/440; 428/535; 428/541

(58) Field of Classification Search .................. 428/541, 428/537.1, 311.71, 480, 481, 482, 535, 540; 427/427.1, 427.7, 440, 254, 297, 322, 324, 427/325, 326, 350, 351, 386, 393, 397, 399, 427/408, 421.1, 430.1, 439; 106/15.05, 18; 536/30, 32, 36, 37, 58, 63, 64, 110, 115, 536/119

See application file for complete search history.

(56) References Cited

U.S. PATENT DOCUMENTS 4,592,962 A * 6/1986 Aoki et al. .................... 428/541
4,832,987 A    5/1989 Ueda et al.
(Continued)

FOREIGN PATENT DOCUMENTS

EP    190576 A2    8/1986
(Continued)

OTHER PUBLICATIONS

Li, Jian-Zhang et al. "Chemical modification of wood by anhydrides without solvents or catalysts", J Wood Sci 46:215-221 (2000).*

(Continued)

*Primary Examiner* — Michael Cleveland
*Assistant Examiner* — Alexander Weddle
(74) *Attorney, Agent, or Firm* — Oblon, Spivak, McClelland, Maier & Neustadt, L.L.P.

(57) ABSTRACT

Process for the chemical treatment of lignocellulose materials, in particular of at least one piece of wood, characterized in that said materials are subjected to impregnation by a chemical agent comprising hydrocarbonaceous chains, this agent being chosen from mixed anhydrides, except for the mixed anhydride of acetic/benzoic acid, said agent being suitable for providing covalent grafting of a plurality of hydrocarbonaceous chains to said materials.

18 Claims, 1 Drawing Sheet

U.S. PATENT DOCUMENTS

| | | | |
|---|---|---|---|
| 5,550,225 | A | 8/1996 | Philippe |
| 6,146,710 | A | 11/2000 | Symons |
| 6,235,346 | B1 | 5/2001 | Barnisin, Jr. |
| 6,248,879 | B1 | 6/2001 | Anderson et al. |
| 6,406,749 | B1 | 6/2002 | Symons |
| 6,426,118 | B2 | 7/2002 | Barnisin, Jr. |
| 2001/0026841 | A1 | 10/2001 | Barnisin, Jr. |
| 2004/0258941 | A1 | 12/2004 | Neogi et al. |
| 2005/0163935 | A1 | 7/2005 | Magne et al. |
| 2006/0269684 | A1 | 11/2006 | Presnell et al. |

FOREIGN PATENT DOCUMENTS

| | | |
|---|---|---|
| WO | WO 03/084723 | 10/2003 |

OTHER PUBLICATIONS

Bernard S.W. Dawson et al., Acylation of Radiata Pine Sapwood, "Reactivity of Radiata Pine Sapwood Towards Carboxylic Acid Anhydrides", (1999) pp. 195-198.

Li, Jian-Zhang et al. "Chemical modification of wood by anhydrides without solvents or catalysts", J Wood Sci 46:215-221 (2000).

Vaca-Garcia, C. et al. "Cellulose esterification with fatty acids and acetic anhydride in lithium chloride/N.Ndimethylacetamide medium", JAOCS, vol. 75, No. 2, 315-319 (1998).

Dawson, Bernard S.W. et al. "Reactivity of radiate pine sapwood towards carboxylic acid anhydrides", Chemical Abstracts Service. vol. 130. No. 20. XP002222940 (1999).

J. Peydecastaing et al, *Molecular Crystals and Liquid Crystals*, "NIR Study of Chemically Modified Cellulosic Biopolymers", 2006, 448, 717-724, Chemical Abstract 145:403600.

F. Aloulou et al, *Separation and Purification Technology*, "Modified cellulose fibres for adsorption of organic compound in aqueous solution", 2006, 332-342, Chemical Abstract 146:86434.

V. Kon'Shin et al, *Izvestiya Vysshikh Uchebnykh Zavedenii, Lesnoi*, "Study of acylation of lignocellulose materials by mixture of carboxylic acid-thionyl" 2003, 4, 92-98, Chemical Abstract 141:316027.

A. Neogi et al, U.S. Pat. Appl. Publ., "Method for esterifying hydroxyl groups in wood", Chemical Abstract 142:58491.

A. Papadopoulos et al, "Efficacy of linear chain carboxylic acid anhydrides as wood protection chemicals", IRG/WP 02-20395.

C. Hill et al, "The kinetics of anhydride modification reactions of wood. Experimental results theoretical modeling", IRG/WP 98-40125.

* cited by examiner

WOOD TREATED BY IMPREGNATION WITH MIXED ANHYDRIDES

CROSS REFERENCE TO RELATED APPLICATIONS

This application is a division of U.S. patent application Ser. No. 10/510,226 (now U.S. Pat. No. 7,790,239), which is the U.S. national stage of International Application No. PCT/FR03/01110, filed Apr. 9, 2003, the disclosures of which are incorporated herein by reference in their entireties. This application claims priority to French Patent Application No. 02/04448, filed Apr. 10, 2002, the disclosure of which is incorporated herein by reference in its entirety.

BACKGROUND

The present invention relates to a process for the treatment of lignocellulose materials, in particular wood, and to a material obtained by this process.

It is targeted more particularly at a process for protecting wood which makes it possible to confer a hydrophobic nature on it, in order to enhance its durability and its dimensional stability.

It is known that, in the natural state, wood or more specifically food fibers which are in contact with a wet atmosphere have a tendency to soak up water. This absorption of water is accompanied by swelling.

Drying can be carried out to remove this water. However, although the drying stage makes it possible to remove the water from the wood, it does not in any way modify its natural hydrophilic nature, with the result that the piece of wood is again capable of reabsorbing the water removed during the drying when this piece is again in a wet environment.

In order to reduce, indeed even eliminate, the hydrophilic nature of the wood and thus to confer on it long-term (conventionally about ten years) dimensional stability, treatment techniques have been sought.

Among these, two main families may be noted, which families are differentiated into physical processes of heat treatment (generally at temperatures of greater than 150° C.) and physicochemical treatment processes, generally at temperatures of less than 120° C.

The present invention is concerned with physicochemical treatment processes.

These physicochemical treatments include processes, known in particular from several publications, Arni et al., (Arni, 1961) ; Matsuzaki et al., which make it possible to synthesize mixed esters from a trifluoroacetic medium. These processes are not viable industrially because of the use of toxic solvent and toxic catalyst.

Additional studies carried out on wood sawdust have demonstrated that the esterification in the presence of a strong acid catalyst (adding more to the intrinsic acidity of the medium) makes it possible to confer a hydrophobic nature on this sawdust. These studies formed the subject of the following publication: Vaca-Garcia C. and Borredon M. E., 1999, Solvent-free fatty acylation of cellulose and lignocellulosic wastes. Part 2: reactions with fatty acids, Bioresource Technology, 70, 135-142.

The major disadvantages [lacuna] this process in the presence of an acid catalyst are the loss in mass of the wood sawdust, this loss in mass resulting from decomposition of the biopolymers constituting the sawdust. A change in color of the sawdust after treatment may also be observed.

A technique similar to the above cannot be applied to a piece of wood. This is because it has been found that hemicellulose molecules and cellulose are partially hydrolyzed, which results in a decrease in the molecular weight through the formation of oligomers and in a decline in the mechanical properties, and also in a deterioration in the appearance of the treated piece of wood.

SUMMARY

The present invention aims to overcome these disadvantages by providing a process which confers a hydrophobic nature on bulk wood while guaranteeing dimensional stability over time, without resulting in the creation of cracks, crackling, splits or a change in color.

A subject matter of the present invention is thus a process for the chemical treatment of lignocellulose materials, in particular of at least one piece of wood, which is characterized in that said materials are subjected to impregnation by a chemical agent comprising hydrocarbonaceous chains, this agent being chosen from mixed anhydrides, except for the mixed anhydride of acetic/benzoic acid, said agent being suitable for providing covalent grafting of a plurality of hydrocarbonaceous chains to said materials.

By virtue of these arrangements, the protection at the surface and at the core of the lignocellulose material, in particular wood, is improved by modification of its hydroxyl functional groups.

In preferred embodiments of the invention, it is optionally possible to have recourse, in addition, to one and/or other of the following arrangements:
- the grafting is carried out by a process of esterification of said lignocellulose materials using a chemical agent chosen from organic anhydrides,
- the treatment is carried out at a temperature between ambient temperature and 150° C. and preferably between 100 and 140° C.,
- the organic anhydride is a mixed anhydride,
- the mixed anhydride comprises a first hydrocarboneuous chain R and a second hydrocarbonaceous chain $R_1$,
- R represents a $C_2$ to $C_4$ carboxylic acid and $R_1$ is a $C_6$ to $C_{24}$ fatty acid, these acids being saturated or unsaturated,
- $R_1$ represents a $C_2$ to $C_4$ carboxylic acid and R is a $C_6$ to $C_{24}$ fatty acid, these acids being saturated or unsaturated,
- the mixed anhydride is the mixed anhydride of acetic/octanoic acids,
- the impregnation is carried out in the presence of a basic catalyst,
- the impregnation is carried out in the presence of a neutral catalyst,
- the impregnation is carried out in the presence of a weak acid catalyst,
- the impregnation is carried out in the absence of catalyst,
- the impregnation of the lignocellulose materials is carried out by a dipping process,
- the impregnation of the lignocellulose materials is carried out by a spraying process,
- the impregnation of the lignocellulose materials is carried out in an autoclave,
- the treatment process is carried out on a piece of wood, the species of which is chosen from, in particular, oak, pine, fir, curupixa or eucalyptus.

According to another aspect of the invention, the latter is also targeted at a piece of wood treated according to the process targeted above, which is characterized in that the lignocellulose fibers are homogeneous and exhibit a smooth appearance.

In preferred embodiments of the invention, it is optionally possible to have recourse, in addition, to one and/or other of the following arrangements:

the degree of absorption of the treated lignocellulose fibers is essentially in the region of 3.5%, the degree of swelling of the treated lignocellulose fibers is substantially in the region of 3.5%.

Other characteristics and advantages of the invention will become apparent in the course of the following description of one of its embodiments, given as non-limiting example, with regard to the appended drawings.

DETAILED DESCRIPTION OF EXEMPLARY EMBODIMENTS

Figure 1:
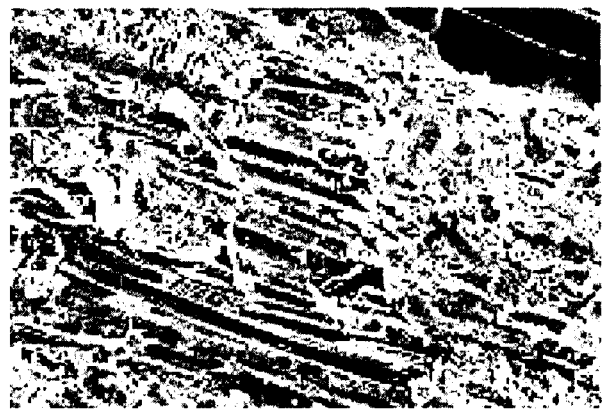
FIG. 1 is a view taken with a scanning microscope (SEM) of a sample of untreated wood; it may stand as reference.

According to a preferred embodiment of the process which is a subject matter of the invention, this process consists in impregnating lignocellulose materials, such as, in particular, at least one piece of wood, with a chemical agent comprising hydrocarbonaceuous chains, said agent being suitable for providing covalent grafting of a plurality of hydrocarbonaceous chains to said materials.

The term "hydrocarbonaceous chain" is understood to mean any heteroaliphatic, heteroaromatic, aliphatic or aromatic chain.

This impregnation is carried out a temperature between ambient temperature and 150° C. and preferably between 100 and 140° C.

This chemical agent is chosen from organic anhydrides and preferably from mixed anhydrides.

A stage of preparation of the mixed anhydride is carried out before the stage of impregnation of said lignocellulose materials (for example, at least one piece of wood) with the chemical agent.

According to a first method: from an acid chloride and a carboxylic ester according to the following reaction:

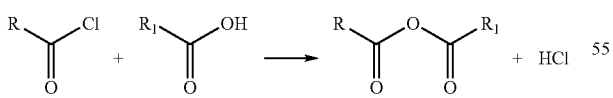

According to an alternative form of the first method, which consists in switching the positions of R and of $R_1$:

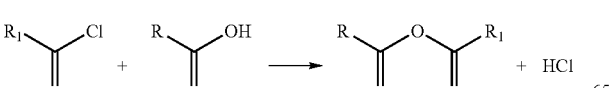

According to a second method: from an acid chloride and a carboxylic acid salt according to the following reaction:

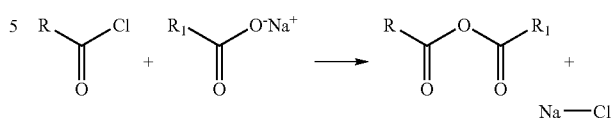

According to a third method: from a linear carboxylic acid anhydride and a fatty acid according to the following reaction:

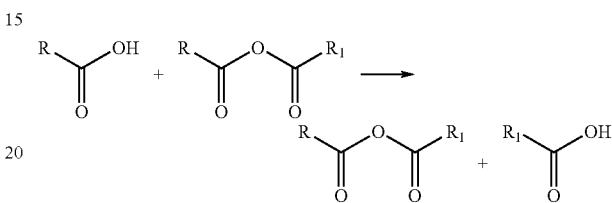

The R and $R_1$ radicals are aliphatic chains of different lengths. By way of non-limiting example, it is assumed that R is shorter than $R_1$.

R represents, by an example, a $C_2$ to $C_4$ carboxylic acid (acetic acid, propionic acid or butyric acid, while $R_1$ is a $C_6$ to $C_{24}$ fatty acid, these acids being saturated or unsaturated (hexylic acid, octanoic acid or oleic acid, for example).

The mixed anhydrides can be used pure or as a mixture and, in this case, originate result from a mixture of different carboxylic acids, from which the synthesis of the desired mixed anhydride is carried out.

The mixed anhydride obtained by at least one of the above-mentioned methods is then used to impregnate a piece of wood so as to graft the mixed anhydride (for example, acetic/octanoic anhydride) to said piece of wood, this grafting comprising an esterification of the wood according to the following reaction:

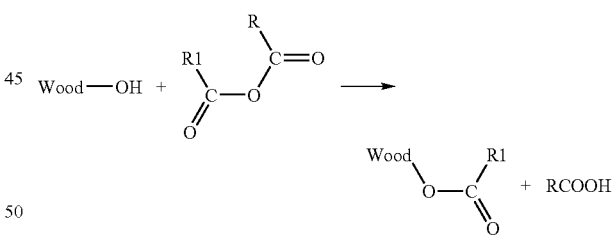

or vice versa with regard to the role between R and R1

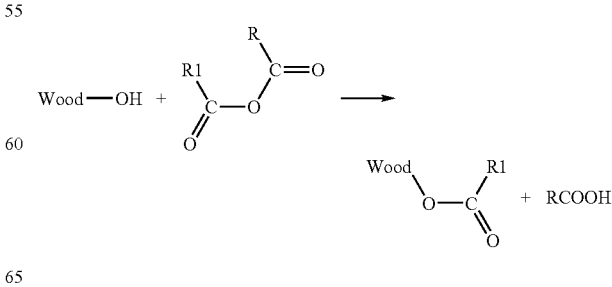

Other esterification methods can also be used according to the reactions envisaged below:

Starting from an acid chloride, this reaction is fast but the evolution of HCl constitutes a major disadvantage.

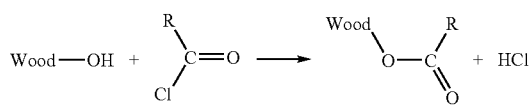

By way of example, the acid chloride is chosen from octanoyl chloride or acetoyl chloride.

Starting from a ketene, the reactants are expensive, however, which limits the industrial advantage.

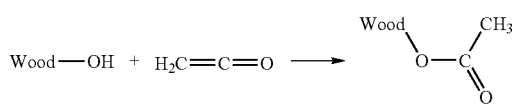

By way of example, this reaction can be combined with, for example, octanoyl chloride.

Starting from carboxylic acids, this reaction nevertheless exhibits a low reactivity and requires the use of coreactants: Pyridine, DCC, TsCl or TFAA (DCC:N,N-dicyclohexylcarbodiimide; TsCl: p-toluenesulfonyl chloride; TFAA:trifluoroacetic anhydride).

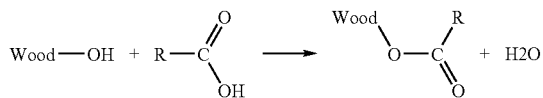

By way of examples, the carboxylic acids used are chosen from acetic acid or octanoic acid.

Starting from carboxylic acid esters (for example, methyl octanoate or methyl acetate), it may be observed, however, that, if R is $CH_3$, evolution of (toxic) methanol occurs.

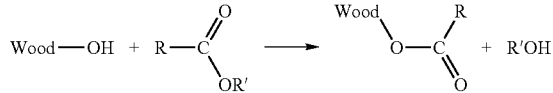

The wood mixed esters can be obtained either in a single stage, with a mixture of the reactants chosen from those presented above, or in 2 stages, either by using the same type of reaction twice, or with two reactions from two different families.

In addition, according to one characteristic of the invention, these esterification reactions can take place in the absence of catalyst or in the presence of a basic or neutral catalyst (such as, for example, calcium carbonate, sodium carbonate, potassium carbonate, fatty acid salt, and the like) or with a weak acid catalyst or with a strong acid catalyst, the harmful effects of which on the wood are minimized by the use of very dilute concentrations.

EXAMPLES

An implementational example of the process according to the invention will be given below:

Example 1: One mole of acetic anhydride was added to one mole of octanoic acid. The mixture was heated with stirring at 140° C. for 30 minutes. A piece of wood with dimensions of 10×10×10 cm was then immersed in the reaction mixture and the combined contents were heated at 140° C. for 1 hour. The piece of wood was then drained of superficial water and dried in a fan oven.

Example 2: One mole of acetic anhydride was added to one mole of octanoic acid. The mixture was stirred at ambient temperature for 60 minutes. A piece of wood with dimensions of 10×10×10 cm was then immersed in the reaction mixture for 5 minutes and then drained of superficial water. The piece of wood was placed in an oven at 120° C. for 1 hour.

A major advantage of the present invention consists in using a non-toxic mixed anhydride of vegetable origin rather than compounds of petrochemical origin.

This specific choice favors the industrial implementation of the invention, as it simplifies treatments aimed at protecting the environment.

Whatever the treatment process used, it is advisable to be able to find a posteriori the signature of this treatment on the lignocellulose material (in our specific case, a piece of wood).

Various methods are envisaged which make it possible to characterize the treatment which the lignocellulose material has been subjected to, namely the determination of the presence of different hydrocarbonaceous chains bonded via ester functional groups and the presence or absence of a catalyst (and its type).

A method which makes it possible to determine the presence of hydrocarbonaceous chains consists in treating a sample originating from the piece of wood with an NaOH solution in order to hydrolyze the ester functional groups and to convert the hydrocarbonaceous chains to carboxylic acid. The latter are subsequently identified by conventional chromatographic methods, such as HPLC, GC, and the like.

An example of these methods consists in starting from a piece of wood or from a lignocellulose material, the hydroxyl functional groups of which have been acylated by at least two different hydrocarbonaceous agents, giving rise to mixtures of esters, for example acetates and octanoates of lignocellulose material.

This mixture of esters can be characterized in the following way: A sample of wood or lignocellulose material treated by the claimed process is ground to a particle size of at least 80 mesh and is then introduced into a flask containing an aqueous ethanol solution (70%). After stirring for at least one hour, a sufficient amount of an aqueous NaOH solution (0.5 M) is added and stirring is continued for 72 h in order to achieve complete saponification of the ester functional groups. After filtering and separating the solid residue, the liquid is acidified to pH 3 with an aqueous HCl solution (1 M) in order to convert the hydrocarbonaceous compounds to the corresponding carboxylic acids. The liquid can subsequently be analyzed by gas chromatography (GC) or by high performance liquid chromatography (HPLC) in order to separate and identify the various carboxylic acids corresponding to the ester functional groups present in the wood or lignocellulose material treated.

Methods which make it possible to identify the type of catalyst will be given below.

Thus, a first method consists in determining the amount of extractables. This method makes it possible to observe the influence of the various treatments on the extractables of the wood (initially present or resulting from the decomposition of the wood). The treated and then micronized wood is subjected to extractions with several solvents of different polarities: Water, ethanol, acetone, and cyclohexane. The extractions are carried out using a Soxhlet device. The amounts of extractables of the treated wood samples, after extraction in a Soxhlet with various solvents, are collated in the table below.

|  | Loss in mass (%) after extraction | | | |
|---|---|---|---|---|
|  | Water | Ethanol | Acetone | Cyclohexane |
| Without catalysis | 14.8 | 11.9 | 12.2 | 6.3 |
| Basic catalysis | 17.1 | 16.2 | 10.6 | 1.8 |
| Strong acid catalysis | 25.3 | 21.7 | 19.0 | 4.8 |

As may be seen, whatever the extraction solvent. These results confirm the visual impressions: Treatment by strong acid catalysis (0.3 mol% $H_2SO_4$), which causes the most decomposition and which results in the formation of the largest amount of extractable compounds at the end of the reaction. For large amounts of strong acid (0.3 mol%), the piece of wood darkens and has a tendency to disintegrate and to exhibit defects in appearance.

On the microscopic scale, the cell wall of the fibers is damaged because of the acid catalysis.

Figure 2:
FIG. 2 is a view taken with a scanning microscope (SEM) of a sample of wood which has been subjected to the process which is a subject matter of the invention, in the presence of a strong acid catalyst.

Thus, in comparison with FIG. 1 and from a qualitative viewpoint, it may be observed, with regard to FIG. 2, that the surface of the wood appears to have been smoothed by the treatment, this surface of the wood is homogeneous. The fibers of the wood (lignocellulose fibers) visible under the microscope appear to be intact compared to those in FIG. 1. The product appears, on the one hand, to have a kind of action of stripping the surface, but also makes possible homogenization of the surface by virtue of the grafting. This is because the grafted chains are capable of protecting the fibers, making it impossible to see them under the microscope.

Figure 3:
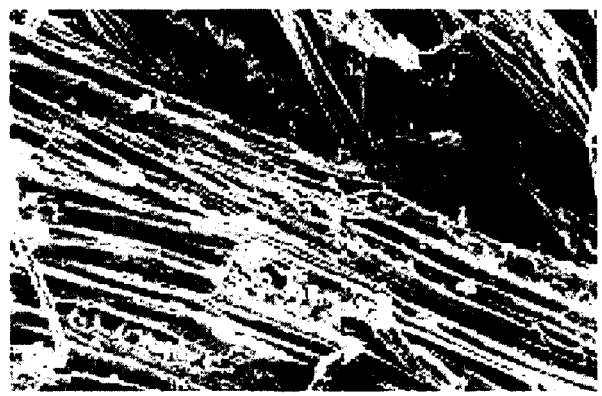
FIG. 3 is another view taken with a scanning microscope (SEM) of a sample of wood which has been subjected to the process which is a subject matter of the invention, in the presence of a strong acid catalyst.

Likewise with regard to FIG. 3, the lignocellulose fibers appear to be exposed. The presence of product is much less marked than above (FIG. 2); this is logical as the photograph exhibits the interior of a block treated by the process of invention. The shredding is due either to the treatment or, probably, to the tearing of the fibers during cutting.

From a quantitative viewpoint, a table is given below in which the values of absorption and of swelling for treated and untreated lignocellulose fibers are stated.

|  | Untreated fibers | Treated fibers |
|---|---|---|
| Absorption in % | 16 | 3.5 |
| Swelling in % | 6.5 | 3.5 |

A second method comprises an analysis of the constituents of the wood. Depending on the type of medium with which the wood is treated, the biopolymers of the wood do not all undergo the same decompositions. The composition of the treated wood may therefore vary according to the treatment. This method is referred to a the "ADF-NDF" method and it makes it possible to find out the proportions of cellulose C, of hemicelluloses H, of lignins L, and of inorganic matter IM.

The data relating to the analysis of the composition of oak wood treated with the acetic/octanoic mixed anhydride with various types of catalysts are collated in the table below. The esterified samples were saponified according to the protocol for the analysis of wood mixed esters and were then washed by extraction with water using a Soxhlet device before being analyzed by the ADF-NDF technique. This technique is described in the reference (Acid Detergent Fiber, Neutral Detergent Fiber), Van Soest P. J. and Wine R. H., Determination of lignin and cellulose in acid-detergent fiber with permanganate. J. Ass. Offic. Anal. Chem., 51(4), 780-785 (1968).

| Nature of the treatment | Catalyst | Extractables (%) | Cellulose (%) | Hemicelluloses (%) | Lignin (%) | Various products (%) | Ash (%) |
|---|---|---|---|---|---|---|---|
| Untreated wood | — | 5.0 | 50.9 | 17.6 | 20.5 | 5.4 | 0.6 |
| Strong acid catalysis | 0.3 mol % $H_2SO_4$ | 22.4 | 49.7 | 14.7 | 8.5 | 4.4 | 0.3 |
| Basic catalysis | 0.3 mol % $Na_2CO_3$ | 16.9 | 40.6 | 16.4 | 20.1 | 5.7 | 0.3 |
| Without catalysis | — | 12.5 | 41.4 | 17.5 | 17.1 | 10.8 | 0.7 |

This analysis therefore makes it possible to distinguish a treatment with strong acid catalysis from the claimed treatments. This is because a larger and significant decrease in the amount of lignin and hemicelluloses is observed. Furthermore, the amount of extractables using the Soxhlet with water is the greatest.

The invention claimed is:

1. A piece of wood, obtained by a process comprising impregnating the piece of wood with a chemical agent comprising hydrocarbonaceous chains:
    wherein:
    the agent comprises a mixed anhydride, given by the formula:

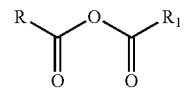

where R is a first hydrocarbonaceous chain and $R_1$ is a second hydrocarbonaceous chain different from the first hydrocarbonaceous chain, except that when either of R or $R_1$ is a methyl group, the other of R and $R_1$ is not a phenyl group;
as a result of impregnating with the agent, a plurality of the hydrocarbonaceous chains are covalently grafted to lignocellulose of the piece of wood; and lignocellulose fibers of the piece of wood are homogeneous and exhibit a smooth appearance.

2. The piece of wood of claim 1, wherein the covalent grafting is carried out by esterification of the lignocellulose material with the agent.

3. The piece of wood of claim 1, wherein the impregnating is carried out at a temperature between ambient temperature and 150° C.

4. The piece of wood of claim 1, wherein the impregnating is carried out in the presence of a catalyst.

5. The piece of wood of claim 1, wherein:
R is a C1 to C3 hydrocarbonaceous chain;
R1 is a C5 to C23 hydrocarbonaceous chain; and
the carboxylic acid and fatty acid are saturated or unsaturated.

6. The piece of wood of claim 1, wherein R is a methyl group, and R1 is a heptyl group.

7. A piece of wood, obtained by a process comprising impregnating the piece of wood with a chemical agent comprising hydrocarbonaceous chains:
wherein:
the agent comprises a mixed anhydride, given by the formula:

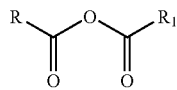

where R is a first hydrocarbonaceous chain and R1 is a second hydrocarbonaceous chain different from the first hydrocarbonaceous chain, except that when either of R or R1 is a methyl group, the other of R and R1 is not a phenyl group;
as a result of impregnating with the agent, a plurality of the hydrocarbonaceous chains are covalently grafted to lignocellulose of the piece of wood; and
the piece of wood exhibits a degree of absorption of about 3.5%.

8. The piece of wood of claim 7, wherein the covalent grafting is carried out by esterification of the lignocellulose material with the agent.

9. The piece of wood of claim 7, wherein the impregnating is carried out at a temperature between ambient temperature and 150° C.

10. The piece of wood of claim 7, wherein the impregnating is carried out in the presence of a catalyst.

11. The piece of wood of claim 7, wherein:
R is a C1 to C3 hydrocarbonaceous chain;
R1 is a C5 to C23 hydrocarbonaceous chain; and
the carboxylic acid and fatty acid are saturated or unsaturated.

12. The piece of wood of claim 7, wherein R is a methyl group, and R1 is a heptyl group.

13. A piece of wood, obtained by a process comprising impregnating the piece of wood with a chemical agent comprising hydrocarbonaceous chains:
wherein:
the agent comprises a mixed anhydride, given by the formula:

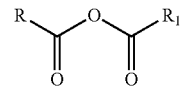

where R is a first hydrocarbonaceous chain and R1 is a second hydrocarbonaceous chain different from the first hydrocarbonaceous chain, except that when either of R or R1 is a methyl group, the other of R and R1 is not a phenyl group;
as a result of impregnating with the agent, a plurality of the hydrocarbonaceous chains are covalently grafted to lignocellulose of the piece of wood; and
the piece of wood exhibits a degree of swelling of about 3.5%.

14. The piece of wood of claim 13, wherein the covalent grafting is carried out by esterification of the lignocellulose material with the agent.

15. The piece of wood of claim 13, wherein the impregnating is carried out at a temperature between ambient temperature and 150° C.

16. The piece of wood of claim 13, wherein the impregnating is carried out in the presence of a catalyst.

17. The piece of wood of claim 13, wherein:
R is a C1 to C3 hydrocarbonaceous chain;
R1 is a C5 to C23 hydrocarbonaceous chain; and
the carboxylic acid and fatty acid are saturated or unsaturated.

18. The piece of wood of claim 13, wherein R is a methyl group, and R1 is a heptyl group.

* * * * *